United States Patent [19]

Benoit et al.

[11] 4,422,714

[45] Dec. 27, 1983

[54] ELLIPSOIDAL OPTICAL COUPLING DEVICE

[75] Inventors: Pierre Benoit, Cortaillod; Jean-Paul Pellaux, Neuchatel; Gilbert Widmer, Le Landeron, all of Switzerland; Betty Kerllenevich, Bahia Blanca, Argentina; Andre Coche, Strasbourg, France

[73] Assignee: Cables Cortaillod S.A., Switzerland

[21] Appl. No.: 245,647

[22] PCT Filed: Sep. 12, 1980

[86] PCT No.: PCT/CH80/00103

§ 371 Date: Mar. 17, 1981

§ 102(e) Date: Mar. 17, 1981

[30] Foreign Application Priority Data

Sep. 14, 1979 [CH] Switzerland ............... 8328/79
Jun. 16, 1980 [CH] Switzerland ............... 4606/80

[51] Int. Cl.³ ............................................. G02B 5/172
[52] U.S. Cl. .............................. 350/96.15; 250/577; 356/136
[58] Field of Search ............... 350/96.15, 96.16, 96.18, 350/96.19, 3.72, 330, 331 R, 350 R, 314, 315; 356/135, 136, 137; 250/577

[56] References Cited

U.S. PATENT DOCUMENTS

| 3,886,544 | 5/1975 | Narodny ............... 350/96.15 X |
| 4,094,578 | 6/1978 | DiVita et al. .......... 350/96.15 |
| 4,261,640 | 4/1981 | Stankos et al. ........ 350/96.15 |
| 4,274,705 | 6/1981 | Miller .................... 350/96.15 |

OTHER PUBLICATIONS

Miller et al., "Feasibility Demonstration of Fiber-Optic Digital Status Monitoring Devices," *Final Report on Contract N00019-77-C-0039*, Section 3, pp. 18–32, Mar. 1978.

Soref, "Fiber-Optic Switching With Liquid Crystals," *Conf. Proceedings of SPIE*, Washington, D.C., Apr. 17–18, 1979, pp. 124–132.

*Primary Examiner*—John D. Lee
*Attorney, Agent, or Firm*—Lerner, David, Littenberg, Krumholz & Mentlik

[57] ABSTRACT

An optical coupling device wherein at least two light conductors are coupled through the intermediary of a transparent block in the shape of a half-ellipsoid on whose foci converge the end sections of the two light conductors. A light beam emerging from one conductor is reflected and transforms itself into a beam converging on the end of the second conductor. A slot permits the introduction of a liquid-crystal attenuating device connected to an alternating voltage source.

22 Claims, 10 Drawing Figures

ELLIPSOIDAL OPTICAL COUPLING DEVICE

The present invention has as its object an optical coupling device with at least two light conductors.

The known optical coupling devices have the shortcoming of comprising, along the path of the light beams, interfaces between the transparent media. The presence of these interfaces has the effect of perturbing the conditions of propagation of the light beams and of causing a generally undesirable attenuation of the transmitted light intensity.

Further, these devices consist of mechanical assemblies of several different pieces, said assemblies being difficult to realize with all the precision necessary and being, moreover, subject to a substantial risk of misalignment when they are subjected to shocks, vibrations or repeated temperature changes.

The invention has precisely as its purpose the elimination of these shortcomings by furnishing an optical coupling device of very great precision, free of the risk of misalignment, and without interface along the path of the light beams.

To this effect, the device according to the invention is characterized by the face that it comprises a solid body at least a portion of which consists of half-ellipsoid of revolution made of a material transparent at least in the wavelength range of the light transmitted by these light conductors. The end of one of these light conductors is placed at one of the foci of this half-ellipsoid, with the end of another of these conductors being placed at the other focus. The optical axes of the two conductors whose ends have been placed at the foci of the half-ellipsoid are oriented in such a way that a divergent light beam emitted by one of these conductors is transformed, after having undergone a total reflection inside the half-ellipsoid, at the interface between the latter and the ambient medium, into a beam converging on the end of the other conductor.

Thus, in this device the principal working element consists of a compact transparent mass in a single piece which can be readily realized by simple casting of a liquid or pastry material such as a molten thermoplastic synthetic resin or a precursor mixture of a thermosetting synthetic resin, and by final hardening of the piece thus obtained.

The invention also has an object the use of this device for detecting a change in the medium with which the convex face of the half-ellipsoid of revolution is in contact, or as a light attenuator, or as an electro-optical switch.

The first use mentioned constitutes an entirely new process which differs from the previously known detection processes by the fact that it completely eliminates the necessity of the production and transmission of electrical detection or measuring signals thanks to the replacement of these signals by purely optical signals. This presents numerous advantages, notably that of eliminating any risk of fire or explosion in the case where the medium in which a change is to be detected is a flammable substance such as a liquid hydrocarbon.

The use as a light attenuator or as an electro-optical switch has the advantage of doing away with any mechanical intervention for modifying the light beam.

The invention will be better understood in the light of the detailed description which is to follow and by making reference to the annexed drawing in which.

Figure 1:
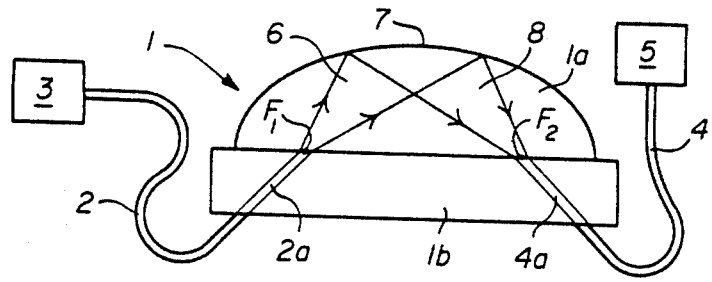
FIG. 1 is a schematic view, in elevation, of a first form of the optical coupling device according to the invention.

The device shown in FIG. 1 comprises a solid body 1 composed of a half-ellipsoid of revolution 1a and of a base piece 1b. The half-ellipsoid of revolution 1a is made of a material transparent at least in the wavelength range of the light transmitted by the light conductors.

A first light conductor 2, for example, a sheathed optical fiber, connected to a light source 3, has its end section 2a embedded in the base piece 1b and converging exactly on one of the foci $F_1$ of the half-ellipsoid 1a. A second light conductor 4, also consisting, for example, of a sheathed optical fiber is connected to a light detector 5 which makes it possible to measure the intensity of the light transmitted by this conductor 4. The end section 4a of the light conductor 4 is likewise embedded in the base piece 1b and converges on the other focus $F_2$ of the half-ellipsoid 1a. The optical axes of the sections 2a and 4a of the respective light conductors 2 and 4 are oriented symmetrically with respect to the median plane between the foci $F_1$ and $F_2$ in such a way that the divergent light beam 6 emitted by the conductor 2 is transformed, after having undergone a total reflection in the region of the interface between the half-ellipsoid 1a and the ambient medium, into a beam converging on the end of the section 4a of the conductor placed at the focus $F_2$. The sections 2a and 4a of the light conductor are advantageously put into place in the base piece 1b before the assembling or the casting of the half-ellipsoid 1a.

The light source 3 consists advantageously of an electro-luminescent diode or of a laser diode. The light detector 5 comprises advantageously a photoelectric cell sensitive in the region of the wavelength of the light emitted by the source 3.

The solid body 1 consists advantageously of a single casting, for example, of a transparent synthetic resin, for example, an epoxy or acrylic resin, comprising the half-ellipsoid 1a and the base piece 1b. However, it is not necessary that the base piece be transparent. The latter may not even be present and may be replaced by any other means adequate to keep the end sections of the light conductors, notably the sections 2a and 4a, in the appropriate fixed position in relation to the transparent half-ellipsoid 1a.

Should the medium in contact with the region 7 of the convex face of the half-ellipsoid 1a along which the incident divergent beam 6 undergoes total reflection change, such that the index of refraction of this medium is altered, for example, by replacement of the initial medium by another medium with a different index of refraction (for example, in the case where the region 7 of the face of the half-ellipsoid 1a initially in contact with air is immersed in a liquid such as mineral oil), with the intensity of the incident beam 6 being kept constant, the intensity of the light transmitted by the coupling device, that is, the intensity of the light captured by the end section 4a of the lead-out conductor 4 undergoes a change corresponding to this change of index.

Figure 2:
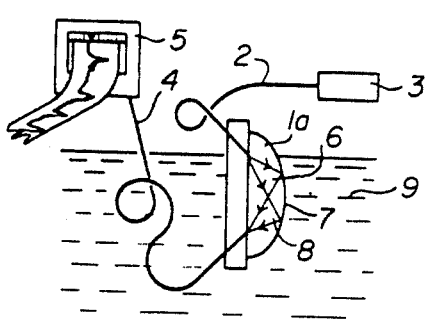
FIG. 2 is a diagram illustrating the use of the device shown in FIG. 1 for detecting a change in the nature of the medium with which the convex face of the half-ellipsoid of revolution is in contact with the object of determining liquid level.

This variation of the intensity of the transmitted light can be turned to account by utilizing the device in a detector. For example, in the case where said variation of the index results from the variation of the level of a liquid, it is possible to detect the variation of the index of refraction which is produced when the region 7 of the half-ellipsoid 1a, initially placed in a fixed position in the air above the level of the liquid, becomes immersed in a liquid due to a rise of the level of said liquid. This liquid level detector may be an apparatus for detecting the level of a mineral oil. By preference, in such an apparatus the median base plane of the half-ellipsoid 1a is placed in a vertical position as shown in FIG. 2. In FIG. 2, the half-ellipsoid 1a is shown in a position partially immersed in the liquid 9 so that the region 7 where the total reflection takes place is entirely in contact with this liquid. In this case, with the intensity of the incident beam 6 being kept constant, the value of the intensity of the reflected beam 8 is lower than the value of this intensity when the region 7 is placed in the air above the level of the liquid 9. This occurs because the index of refraction of the latter region in contact with the liquid has a value which comes closer to that of the index of refraction of the ellipsoid 1a than the index of refraction of air. When the region 7 is withdrawn from the liquid, particularly in the case where this liquid is oily, one observes an abrupt increase in the intensity of the reflected beam 8, an increase which manifests itself by the appearance of a peak exceeding the intensity of the reflected light prior to the immersion of the region 7 in the liquid 9. This is due to the formation of a film of liquid 9 over this region. After the region 7 is withdrawn from the liquid, one observes a progressive diminution of this intensity which tends to finally assume the value corresponding to the total reflection of the region 7 in contact with air. In the opposite case, the decrease of the intensity of the reflected light 8 during the immersion of the region 7 in the liquid 9 makes it possible to detect a rise in the level of this liquid.

Figure 3:
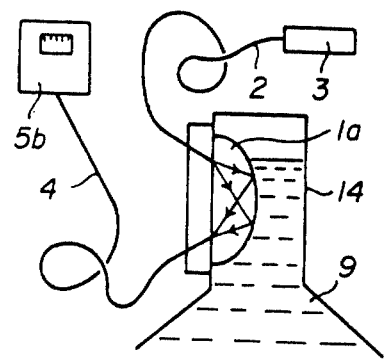
FIG. 3 is a diagram illustrating the use of the device in FIG. 1 for detecting a change in the nature of the medium with which the convex face of the half-ellipsoid is in contact, in the case where this change results from the presence of gas bubbles in a liquid, with the object of detecting the presence of these bubbles.

The diagram in FIG. 3 illustrates the use of the coupling device according to the invention for detecting the presence of a gaseous release in a liquid. In this case, the half-ellipsoid 1a is entirely immersed in the liquid 9 and placed inside a capsule 14 in which the released gas accumulates. In the case where the volume of gas released is greater than the volume of the capsule 14, the abrupt apparition of a liquid signal received by the light detector 5b permits the detection of the presence of the gas. The inside volume of the capsule 14 is, of course, chosen as a function of the gas volume whose presence must be detected, that is, according to the volume of gas which can be tolerated in the liquid 9.

Figure 4:
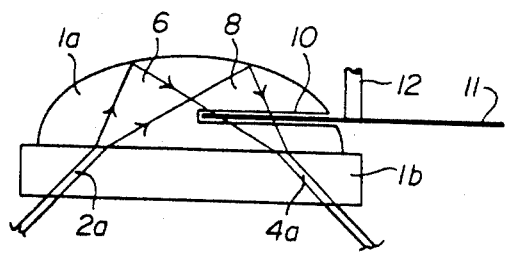
FIG. 4 is a schematic view of a second form of the coupling device according to the invention, again shown in elevation.

The device shown in FIG. 4 has a general layout similar to the one of the device in FIG. 1. It differs from the latter only by the fact that it comprises a slot 10 cut into the half-ellipsoid 1a parallel to the median base plane of the latter and a disk 11 having a plurality of regions (not shown) which have with respect to each other different light absorption properties. The disk 11 is arranged in such a manner that it can rotate around an axis 12 oriented perpendicularly to the median base plane of the half-ellipsoid 1a. Thus, when the disk 11 turns, these different regions are placed successively inside the slot 10 along the path of the reflected beam 8. The different regions of the disk 11 thus function like light intensity filters possessing different optical densities and the device forms in its entirety an optical coupler-attenuator for light conductors.

Figure 5:
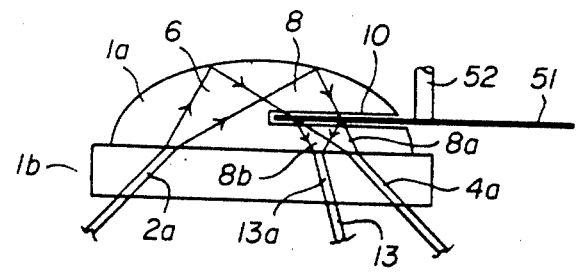
FIG. 5 is a schematic view, still in elevation, of a third form of the device.

The device shown in FIG. 5 is also similar to the devices shown in FIGS. 1 and 4. In particular, like the device in FIG. 4, it comprises a slot 10 parallel to the median base plane of the half-ellipsoid 1a. However, in place of an absorbent rotating disk 11 it is provided with a disk 51 rotating around an axis 52 and carrying several diffraction gratings, for example, four holographic gratings $H_1$, $H_2$, $H_3$ and $H_4$ (FIG. 6) which makes it possible to separate the reflection beam 8 into two partial beams 8a and 8b, one of which (8a) follows the same path as the corresponding initial portion of the beam 8, converging, therefore, on the end of the end section 4a of the optical fiber 4 placed at the focus $F_2$ of the half-ellipsoid 1a, and whose other beam (8b) converges on the end of another optical fiber 13 whose end section 13a is embedded in the base piece 1b of the body 1. The sum of the intensities of the light beams 8a and 8b is equal to the intensity of the reflected beam 8.

Figure 6:
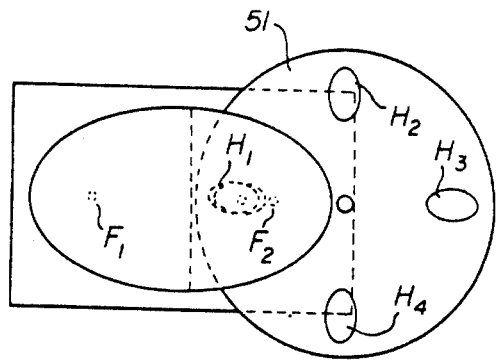
FIG. 6 is a plane view of the device shown in FIG. 5.

The device shown in FIGS. 5 and 6 constitutes a coupler of the so-called "Y-junction" type for light conductors and has, compared to the previously known optical couplers, the advantage of permitting the connection of one light conductor to two other light conductors without perturbing the light propagation conditions in the waveguide. The preparation of the holographic lenses $H_1$ to $H_4$ of this device (the number of these lenses may be more than four, taking into account the dimensions of the region of the reflected beam 8 intersected by the disk 51 and the dimensions of the latter) can be effected either before or after assembling the disk 51. The last-named procedure (formation of the holographic lenses in situ) which has the advantage of considerably simplifying the optical adjustments of the coupler may be similar to the one described in the Swiss Pat. No. 626 729 (Patent Application No. 12 298/78) whose contents are incorporated by reference in the present description.

By using lenses comprising a superposition of diffraction, for example, holographic lenses, it is possible to realize in a manner similar to the realization of the Y-junction coupler shown in FIGS. 5 and 6, a coupler with multiple or star junctions as those skilled in the art would deduce in the light of the description in the aforementioned Swiss patent (Patent Application No. 12 298/78).

The use of a mechanical device such as the rotating filter device described with reference to FIG. 4 requires a cumbersome mechanical setup in order to make it possible to hold the disk in place and to move it. Moreover, the number of regions is of necessity limited and increasing this number inevitably makes the system still more cumbersome.

Figure 7:
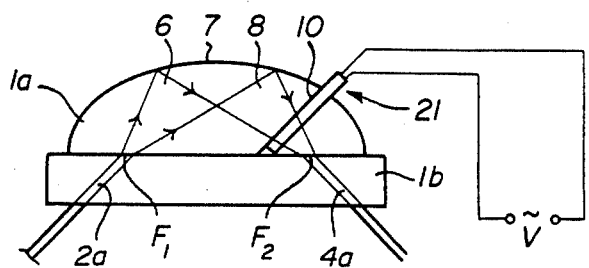
FIG. 7 is a schematic view in cross section of the coupling device equipped with a liquid-crystal light attenuator.
Figure 8:
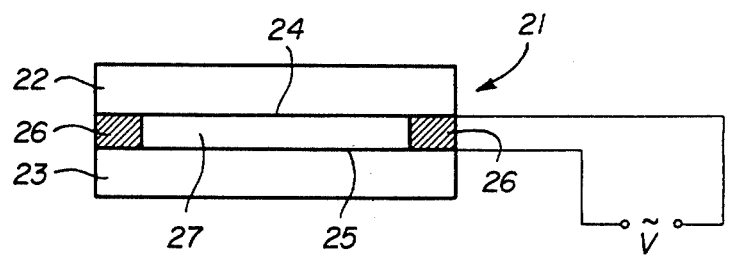
FIG. 8 is an enlarged cross-sectional view of the attenuating device housed in the slot of the coupling device shown in FIG. 7.

The device described below with reference to FIGS. 7 and 8 is intended to remedy these shortcomings by realizing a device of the type mentioned above in which it is possible to obtain at will a partial attenuation or a total obturation of the reflected light without the necessity of having to act mechanically on a filter or an obturator seated in the slot.

With reference to FIG. 7, the optical coupling device is composed of the half-ellipsoid of revolution 1a made of a transparent material and of the base 1b described with respect to FIG. 1. An end section 2a is embedded in the base piece 1b, converging exactly on the focus $F_1$ of the half-ellipsoid 1a. It emits a divergent light beam 6 which, after having undergone a total reflection along the region 7 of the interface between the half-ellipsoid 1a and the ambient medium, is transformed into a convergent beam 8 at the end of the light conductor whose end section 4a converges on the focus $F_2$. The slot 10, cut into the half-ellipsoid 1a at an angle to the median plane of the base 1b makes it possible to introduce a liquid-crystal attenuating or obturating device 21 which is connected externally to an alternating voltage V and is described in more detail with reference to FIG. 8.

FIG. 8 illustrates in greater detail the light-attenuating device 21 which is slipped into the slot 10 of the half-ellipsoid 1a. It is composed essentially of two transparent sheets 22 and 23 rendered conductive along their inner faces 24 and 25 and separated by spacers 26. Between the transparent sheets 22 and 23 there is a nematic liquid-crystal layer 27 which is in contact with the conductive faces 24 and 25 of the transparent sheets 22 and 23. These sheets may consist of two plates of quartz or glass made conductive along their inner faces by metallization or spraying with indium oxide ($In_2O_3$) or tin oxide ($SnO_2$). The conductive inner faces 24 and 25 of the transparent plates 22 and 23 are connected to an alternating voltage source V (shown schematically).

Figure 9:
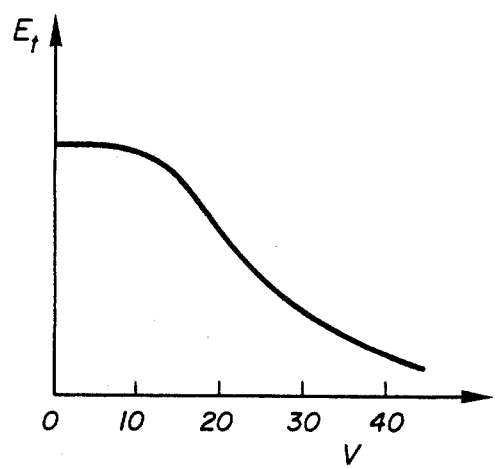
FIG. 9 shows a diagram of the transmission curve of the light passing through the attenuating device according to FIG. 8.

When the liquid-crystal layer 27 consists of a nematic substance with negative dielectric anisotropy, the curve of the light transmission as a function of the potential difference applied to the electrodes 24 and 25 has the appearance shown in FIG. 9. It can be noted that according to the voltage applied the attenuation is larger or smaller, which means that it is possible to obtain a progressive attenuation by modifying the potential difference between the two conductive faces. In practice, the useful attenuation range corresponds to a variation on the order of some tens of volts.

Figure 10:
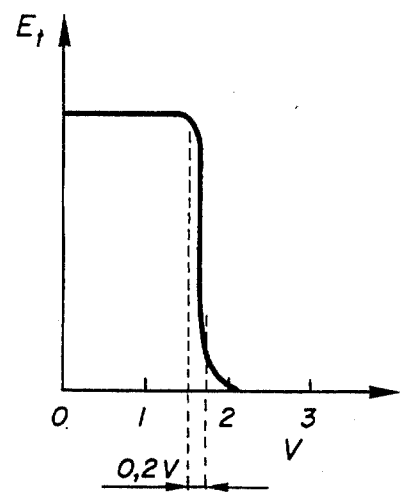
FIG. 10 shows another transmission curve of the light obtained under different experimental conditions.

When the liquid crystal layer consists of a so-called "twisted" nematic, that is, one which has undergone a torsion so that the orientations of its molecules, at the level of the transparent electrodes, are perpendicular, the transmission curve corresponds to the graph in FIG. 10. In this case, the attenuation is very abrupt and the attenuator function in this case is more like a switch. This device operates with polarized light and requires, therefore, the use of a polarizer and an analyzer. It makes it, on the other hand, possible to operate at a very low voltage, on the order of a few volts. The change of state of the liquid crystal which makes it possible to obtain an almost total obturation occurs over a range of a few tenths of a volt, for example, by a modification of the potential difference by 0.2 volt in the case of FIG. 10.

The practical realization of the attenuating device is extremely simple. The thickness of the spacers 26 which can be realized in the form of an annular joint, for example, is of the order of 10 μm. The unit may consist of a tight and interchangeable block which can be introduced into the slot of the half-ellipsoid according to the needs and experimental conditions of its use. This same coupling device can also be used at will with an attenuating device corresponding to the transmission curve in FIG. 9 or with an attenuating device acting more like an obturator and corresponding to the transmission curve illustrated in FIG. 10.

What is claimed is:

1. An optical coupling device for at least two light conductors, comprising a solid body at least a part of which consists of a half-ellipsoid of revolution made of a material transparent at least in the wavelength range of the light transmitted by these light conductors, the outer surface of said half-ellipsoid being placed in an ambient medium, means for positioning the end of one of said light conductors at one of the foci of said half-ellipsoid, second means for positioning the end of a second light conductor at the other focus of said half-ellipsoid, said positioning means orienting the optical axes of the two conductors whose ends have been placed at the foci of the half-ellipsoid in such a way that a divergent light beam emitted by one of these conductors is transformed, after having undergone a total reflection inside said half-ellipsoid, at the interface between said half-ellipsoid and said ambient medium into a beam converging on the end of the other conductor, said half-ellipsoid including a slot formed therein to permit the interposition along the path of said convergent beam of beam modifying means operative to modify a light beam transmitted through said half-ellipsoid.

2. An optical coupling device according to claim 1 wherein said positioning means include a base piece joined to said half-ellipsoid in the median plane containing the foci of the generating ellipse of said half-ellipsoid, and at least two light conductors having their ends embedded in said base piece.

3. An optical coupling device according to claim 1 wherein said slot is substantially perpendicular to the direction of a median ray of said convergent beam.

4. An optical coupling device according to claim 1 wherein said beam modifying means comprises at least one intensity filter.

5. An optical coupling device according to claim 4 wherein said beam modifying means is placed in a slot cut into said half-ellipsoid parallel to the median base plane of said half-ellipsoid.

6. An optical coupling device according to claim 5 wherein said beam modifying means includes a disk having a plurality of regions having, with respect to each other, different light absorption properties, said disk being rotatable around an axis perpendicular to the median base plane of said half-ellipsoid whereby different regions of the disk can be placed successively inside said slot.

7. An optical coupling device according to claim 1 wherein said beam modifying means comprises at least one holographic lens.

8. An optical coupling device according to claim 7 wherein said holographic lens is positioned in a slot cut into said half-ellipsoid, parallel to the median base plane of said half-ellipsoid.

9. An optical coupling device according to claim 7 wherein said holographic lens is designed in such a way that the zero order of diffraction of the holographic lens reconstitutes a first light beam converging toward the end of one light conductor placed at a focus of the ellipse generating said half-ellipsoid, while the first order of diffraction reconstitutes a second light beam converging toward the end of another light conductor.

10. An optical coupling device according to claim 1 wherein said beam modifying means comprises a liquid-crystal light-attenuating device.

11. An optical coupling device according to claim 10 wherein said light-attenuating device includes a liquid-crystal layer formed between two transparent plates made conductive along their inner faces in contact with the liquid crystal, and electric power means for applying a potential difference between said conductive opposite faces.

12. An optical coupling device according to claim 11 wherein said electric power means provides an alternating potential.

13. An optical coupling device according to claim 11 wherein said two plates are metallized on their inner faces.

14. An optical coupling device according to claim 11 wherein said two plates are made conductive utilizing a material selected from the group: indium oxide and tin oxide.

15. An optical coupling device according to claim 11 wherein said liquid-crystal layer includes nematic substances.

16. An optical coupling device according to claim 15 wherein the light transmitted is a polarized light, said liquid crystal layer being sensitive to polarized light to undergo a torsion so that the orientations of the molecules at the level of the respective transparent plates are perpendicular.

17. Use of the device according to any one of the claims 10 to 15, as a means of subduing the light transmitted by the device.

18. Use of the device according to claim 17, as an electro-optical switch.

19. Use of the device according to claim 1, in order to detect a variation in the medium with which the convex face of the half-ellipsoid of revolution is in contact, wherein the light intensity transmitted by the optical coupling device is measured, from the end of one of the light conductors to the end of the other light conductor, before and after variation of the medium while at the same time maintaining the intensity of the incident light.

20. Use according to claim 19, in the case where the said variation, in the medium in contact with the convex face of the half-ellipsoid, results in the variation of the level of a liquid, wherein, after having placed the median base plane of the half-ellipsoid in a vertical position, at least one measure of light intensity corresponding to a level of the liquid is effected, such as the field of the convex face of the half-ellipsoid, on which total reflection is effected of the said divergent light beam, is a least partially immersed in the liquid.

21. Use according to claim 19, wherein the said light intensity measure is effected in a continuous manner, by recording the development, as a function of time, of the values of the light intensity transmitted by the coupling device.

22. Use according to claim 19, in the case where the said variation, in the medium in contact with the convex face of the half-ellipsoid, results in the presence of a gas in a liquid, wherein measures of light intensity are effected after having placed the half-ellipsoid of revolution, with its median plane in a horizontal position, inside a capsule where the gas is collected, this capsule having an internal volume corresponding to the gas volume to be detected.

* * * * *